United States Patent [19]

Maeda et al.

[11] Patent Number: 5,863,550
[45] Date of Patent: *Jan. 26, 1999

[54] CHOLESTASIS AMELIORANT

[75] Inventors: Minoru Maeda; Kumiko Koiso; Shozaburo Sekido, all of Tokyo, Japan

[73] Assignee: Tokyo Tanabe Company Limited, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 530,151

[22] PCT Filed: Feb. 23, 1994

[86] PCT No.: PCT/JP94/00202

§ 371 Date: Dec. 1, 1995

§ 102(e) Date: Dec. 1, 1995

[87] PCT Pub. No.: WO94/22896

PCT Pub. Date: Oct. 13, 1994

[30] Foreign Application Priority Data

Mar. 31, 1993 [JP] Japan ................................ 5-074393

[51] Int. Cl.$^6$ .............................. A61F 2/02; A61K 9/48; A61K 9/20; A61K 31/56
[52] U.S. Cl. ......................... 424/423; 424/451; 424/464; 514/182
[58] Field of Search .................................. 424/423, 451, 424/464; 514/182

[56] References Cited

U.S. PATENT DOCUMENTS 5,260,074  11/1993  Sipos ........................ 424/497
5,500,421  3/1996  Parenti ..................... 514/182

OTHER PUBLICATIONS

Kitani et al., "Tauroursodeoxycholate prevents taurocholate induced cholestasis", Life Sci., 30(6):515–523 (1982).
Hayakawa et al., "Effect of bile acid on cholestasis induced by 17.alpha ethinylestradiol", Chem. Abstr. 108(9):(1988).
Schoelmerich et al., "Taurohyocholate, taurocholate, and tauroursocholate but not tauroursocholate and taurodehydrocholate counteract effects of taurolithocholate in rat liver", Res. Exp. Med. 190(2):121–129 (1990).
Schoelmerich et al., "Tauroursodeoxycholate prevents taurolithocholate–induced cholestasis and toxicity in rat liver", J. Hepatol. 10(3):280–283 (1990).
Zhao et al., "Effects of bile salt supplementation on biliary secretion in estrogen–treated rats", Chem. Abstr. 113(21):189102 (1990).
Yokote M., "Effect of bile acids on experimental intrahepatic cholestasis of the rat", Teikyo Igaku Zasshi 13(2):137–150 (1990).
Abernathy et al., "Drug–induced cholestasis in the perfused rat liver and its reversal by taroursodeoxycholate: an ultrastructural study", Proc, Soc. Exp. Biol. Med., 199(1):54–58 (1992).
Utili et al., "Effect of bile salt infusion on chlorpromazine–induced cholestasis in the isolated perfused rat liver", Proc. Soc. Exp. Biol. Med., 199(1):49–53 (1992).
Minagawa et al., "Cholestasis induced by lithocholate glucuronide. A study with congenital jauniced rats and effects of ursodeoxycholate conjugates", Chem Abstr. 117(15):148401 (1992).
Nakai et al., "Microtubule–independent choleresis and anticholestatic action of cholchicine–treated rat liver", Biochem. J. 288(2):613–617 (1992).
Heuman et al., "Conjugates of ursodeoxycholate protect against cholestasis and hepatocellular necrosis caused by more hydrophobic bile salts: in vivo studies in the rat", Gastroenterology 100(1):201–211 (1991).

*Primary Examiner*—Carlos Azpuru
*Attorney, Agent, or Firm*—Pillsbury Madison & Sutro LLP

[57] ABSTRACT

Disclosed is a cholestasis ameliorant containing tauroursodeoxycholic acid, which is more excellent in solubility than ursodeoxycholic acid, as the active ingredient. The ameliorant is useful for the treatment of intrahepatic cholestasis due to drug-induced hepatopathy, viral hepatitis or the like and the treatment of cholestasis occurring after surgical operation for the treatment of obstructive jaundice.

6 Claims, No Drawings

CHOLESTASIS AMELIORANT

CROSS-REFERENCE TO RELATED APPLICATIONS

This application claims benefit of international application PCT JP94/00282, filed Feb. 23, 1994.

BACKGROUND OF THE INVENTION

1. Field of the Invention

The present invention relates to a cholestasis ameliorant containing tauroursodeoxycholic acid as the active ingredient. Tauroursodeoxycholic acid is a taurine conjugate of ursodeoxycholic acid represented by the following structural formula.

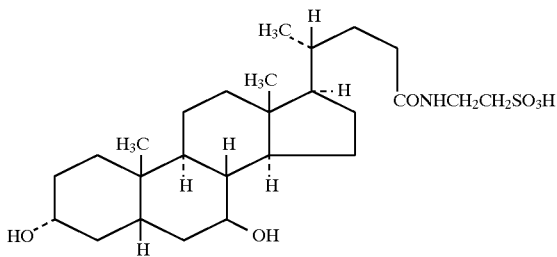

2. Background Information

Cholestasis is a pathological condition where the choleresis, which is one of the important functions of the liver, is suppressed and the bile flow from the liver through the bile duct to the duodenum is reduced, resulting in congestion of biliary components, and it is categorized into extrahepatic obstructive jaundice, which is caused by an apparent mechanical obstruction such as tumor or gallstones, and intrahepatic cholestasis, which occurs with no macroscopically noticeable site of obstruction. Intrahepatic cholestasis is further classified into acute type due to drug-induced hepatitis or viral hepatitis, chronic type represented by primary biliary cirrhosis (PBC), recurrent type occurring familially or during pregnancy and the like and the main clinical symptoms common to all types of intrahepatic cholestasis are severe jaundice and persistent itching.

Steroid and phenobarbital preparations are currently used for the treatment of intrahepatic cholestasis, showing a certain level of, but often insufficient, efficacy.

In patients with obstructive jaundice, biliary drainage techniques such as percutaneous transhepatic cholangio drainage (PTCD), whose purpose is external biliary drainage, are performed but there are quite a few cases where jaundice takes a chronic course because of insufficient biliary drainage.

Since it has recently been reported in Japan and other countries that ursodeoxycholic acid preparations have very high efficacy against intrahepatic cholestasis, development of injectable ursodeoxycholic acid preparations has been hoped for.

However, the solubility of ursodeoxycholic acid is very low and, if it is prepared in an injectable form, the injection would have shortcomings such as causing angialgia because of high pH value.

Therefore, a related substance that is soluble in water and is easy to be prepared into injectable preparations at near-neutral pH has been searched for.

SUMMARY OF THE INVENTION

In the course of research on the effects of ursodeoxycholic acid on various derivatives of bile acids in patients with liver diseases, the present inventors had found that tauroursodeoxycholic acid has ameliorative effect against cholestasis and better solubility in water as compared with ursodeoxycholic acid and that it may be easily prepared into injectable preparations.

According to the present invention, cholestasis ameliorant containing tauroursodeoxycholic acid as the active ingredient are provided.

[BEST MODE FOR CARRYING OUT THE INVENTION]

Tauroursodeoxycholic acid used in the present invention may be a pharmaceutically acceptable salt thereof, and can be produced from ursodeoxycholic acid by the application of well known manufacturing processes of taurine-conjugated bile acids. For instance, it can be produced by reacting an alkyl chlorocarbonate with ursodeoxycholic acid in a non-hydrating solvent in the presence of a basic catalyst and then reacting taurine in an alkaline solution with this solution.

DETAILED DESCRIPTION OF THE INVENTION

<Pharmacological activity>

(Ameliorative effect against cholestasis in rats)

An extra external-biliary fistula was developed in female SD rats under anesthesia and, after bile collection for 30 minutes, estradiol-17β-D-glucuronide (E-17-G) was administered via their femoral veins as a single dose of 10 $\mu$ mole/kg. Immediately after the administration, tauroursodeoxycholic acid was continuously administered over two hours via the femoral veins at a rate of 0.6 $\mu$ mole/min/100 g body weight, and the bile flow was measured serially.

Tauroursodeoxycholic acid inhibited the reduction of the bile flow induced by E-17-G at a rate of 0.3 $\mu$ mole/min/100 g body weight or higher, and this inhibition effect was more marked than that of free ursodeoxycholic acid.

(Protective effect against hepatic injury in mice)

Tauroursodeoxycholic acid was administered to male ICR mice via their caudal veins at a dose within a range of 100 to 1200 $\mu$ mole/kg two hours before and two hours after an administration of α-naphthylisothiocyanate (ANIT) as a single dose of 80 mg/kg. Serum bilirubin concentration, total bile acid concentration and LDH activity were measured two days after the ANIT administration.

Tauroursodeoxycholic acid inhibited the increases of bilirubin concentration, total bile acid concentration and LDH activity induced by ANIT.

(Clinical results of tauroursodeoxycholic acid injection)

[EXAMPLE 1]

Female, 71 years old, 46 kg

In December of 1992, GOT and GPT of this patient began to increase on the third day from the start of drug administration for the treatment of neuralgia and reached 548 U/l and 664 U/l respectively on the 12th day, and the total bilirubin level also increased up to 18.6 mg/dl after discontinuation of the drug administration. Since tylosis of the gallbladder walls was observed by abdominal ultrasonic imaging and there were severe icteric symptoms, this case was diagnosed as cholestasis due to drug-induced hepatopathy.

At a stage when moderate jaundice still remained (total bilirubin: 6.9 mg/dl) and no improvement had been noted in subjective symptoms such as skin itching and epigastric discomfort, tauroursodeoxycholic acid was intravenously injected once a day at a dose of 100 mg for 14 days. As a result, the total bilirubin level, GOT and GPT were decreased to 2.1 mg/dl, 45 U/l and 36 U/l, respectively, and the icteric symptoms as well as the subjective symptoms such as skin itching and epigastric discomfort were disappeared.

[EXAMPLE 2]

Male, 32 years old, 63 kg

The patient, a Japanese San Francisco resident, felt itching of fingers in March 1993, and was diagnosed to suffer from acute viral hepatitis in a medical institution in San Francisco, where he received treatment for a short period. After the patient came back to Japan on April 5 and was hospitalized, tauroursodeoxycholic acid was intravenously administered once a day at a dose of 100 mg for 14 days.

As a result, total bilirubin level of 31.4 mg/dl before the administration was decreased to 13.7 mg/dl and total bile acid level of 21 μmole/l before the administration to 12 μmole/l. Subjective symptoms such as skin itching and anorexia were disappeared with improvement of icteric symptoms from the day after three days of the administration.

[EXAMPLE 3]

Female, 56 years old, 56 kg

This patient had a history of acute hepatitis type A and was diagnosed to suffer from drug-induced hepatopathy based on liver biopsy showing necrosis of pericentrilobular parenchymal cells.

At a stage when moderate jaundice was observed (total bilirubin: 9.0 mg/dl, GOT: 838 U/l, GPT 451 U/l), tauroursodeoxycholic acid was administered once a day at a dose of 300 mg by intravenous drip infusion for 14 days. As a result, the total bilirubin level, GOT and GPT were decreased to 2.8 mg/dl, 171 U/l and 145 U/l, respectively, and no increase was observed in these parameters two weeks after the completion of the administration, showing improvement in icteric symptoms due to cholestasis.

[EXAMPLE 4]

Male, 32 years old, 59 kg

This patient was diagnosed to suffer from cholestasis due to acute viral hepatitis based on results of immunoserological test including GOT of 11600 U/l, GPT of 6300 U/l and total bilirubin level of 7.7 mg/dl and HBV positive result of virological test as well as severe icteric symptoms.

At a stage when jaundice was still severe (total bilirubin: 16.19 mg/dl), tauroursodeoxycholic acid was administered once a day at a dose of 300 mg by intravenous drip infusion for 14 days. As a result, the total bilirubin level, GOT and GPT were decreased to 4.4 mg/dl, 48 U/l and 36 U/l, respectively, icteric symptoms were improved from the day after one week of the administration and subjective symptoms such as skin itching and systemic malaise were disappeared by the 10th day of the administration.

[EXAMPLE 5]

Female, 22 years old, 49 kg

This patient began to feel general malaise in late June 1993 and, since jaundice appeared on Jun. 28, she visited a neighboring clinic and received treatment. In spite of that, jaundice was not improved and she referred to our medical institution on July 5. Based on the results of inspections, the patient was diagnosed to suffer cholestasis due to acute viral hepatitis (type B).

Tauroursodeoxycholic acid was administered by intravenous injection once a day at a dose of 600 mg for 18 days from July 8. As a result, the total bilirubin level was reduced by half after 4 days of the administration and further reduced to almost within the normal range after one week. Other parameters related to the liver function were also improved, and icteric symptoms and general malaise were disappeared.

[EXAMPLE 6]

Male, 55 years old, 60 kg

This patient noticed jaundice in the middle of May 1993 and consulted a doctor. His symptom was diagnosed as obstructive jaundice based on images of enlargement of the bilateral intrahepatic bile ducts and 3–4 cm long irregular stenosis in the choledoch observed in endoscopic retrograde cholangiopancreatography (ERCP) and underwent endoscopic nasotracheal bile duct drainage (ENBD) on May 31.

Because icteric symptoms were not improved, tauroursodeoxycholic acid was intravenously injected once a day at a dose of 100 mg for 22 days. As a result, an apparent increase of bile flow and decrease of the total bilirubin level were observed after one week of the administration with improvement of jaundice and skin itching.

[EXAMPLE 7]

Male, 61 years old, 60 kg

This patient was diagnosed to suffer from pancreatic cancer by ERCP. Immediately after hospitalization, percutaneous transhepatic cholangio drainage (PTCD) was performed and the total bilirubin level showed a temporal decreasing tendency from a maximum of 35 mg/dl but it remained around 15 mg/dl without any further decrease. Concurrently, icteric symptoms and skin itching were continued. Therefore, tauroursodeoxycholic acid was intravenously injected once a day at a dose of 600 mg for 38 days. As a result, the total bilirubin level was decreased to 3.3 mg/dl, the bile flow was increased from the preadministration level of 230 ml/day to 440 ml/day, and icteric symptoms and skin itching were improved.

(Acute toxicity)

The acute toxicity ($LD_{50}$) of intravenously administered tauroursodeoxycholic acid was evaluated in 6-week old male and female CD rats and 8 to 11-month old male and female beagle dogs. The $LD_{50}$ was 600 to 800 mg/kg in male rats and 800 to 1000 mg/kg in female rats.

In beagle dogs, it was 300 to 600 mg/kg for both sexes.

Based on the results shown above, drugs containing tauroursodeoxycholic acid as the active ingredient can be referred to as cholestasis ameliorant with protective effect of hepatocyte.

While the dose of tauroursodeoxycholic acid may be vary depending on age, symptoms and the like of patients, its daily dose for adults may be 50 to 3000 mg, preferably 200 to 1500 mg for oral administration, or 30 to 1200 mg, preferably 100 to 600 mg for intravenous injection and it may be given once or in two divided doses.

The cholestasis ameliorant of the present invention may include various pharmaceutical compositions that contain a pharmaceutical solid or liquid carrier that does not affect tauroursodeoxycholic acid as the active ingredient to an extent that the daily dose of tauroursodeoxycholic acid described above can be maintained. Such pharmaceutical compositions can be provided in the form of tablets, capsules, powder, fine granules, granules, solution, syrup or injection.

Because tauroursodeoxycholic acid, the active ingredient of the present invention, shows high solubility in water, it can be prepared as aqueous injection by using purified water or physiological saline. It is desirable that tauroursodeoxycholic acid is contained at a concentration of 1 to 10% (W/V) in aqueous injection.

[Preparation Example 1]

An injectable preparation containing 6% (W/V) of tauroursodeoxycholic acid was produced by dissolving 60 g of tauroursodeoxy-cholic acid in 1000 ml of physiological saline, filtering the solution through a 0.2 μm membrane filter, filling 5 ml each in ampules, fusion-closing the ampules, and sterilizing by boiling for 30 minutes.

[Preparation Example 2]

An injectable preparation containing 1% (W/V) of tauroursodeoxycholic acid was produced by adding purified water to 10 g of tauroursodeoxycholic acid and 46 g of D-mannitol to make a total volume of 1000 ml and treating the solution in the same manner as Preparation Example 1.

[Preparation Example 3]

An injectable preparation containing 3% (W/V) of tauroursodeoxycholic acid was produced in the same manner as Preparation Example 2 by using 30 g of tauroursodeoxycholic acid and 42 g of D-mannitol.

[Preparation Example 4]

An injectable preparation containing 6% (W/V) of tauroursodeoxycholic acid was produced in the same manner as Preparation Example 2 by using 60 g of tauroursodeoxycholic acid and 37 g of D-mannitol.

[Preparation Example 5]

Tablets containing 300 mg of tauroursodeoxycholic acid were produced by sufficiently mixing 300 g of tauroursodeoxycholic acid and 100 g of lactose to homogeneity, adding magnesium stearate as a lubricant uniformly and making tablets by a tablet machine.

[Preparation Example 6]

Capsules of tauroursodeoxycholic acid were produced by sufficiently mixing 300 g of tauroursodeoxycholic acid and 100 g of lactose to homogeneity and filling the mixture in soft capsules so that each capsule would contain 100 mg of tauroursodeoxycholic acid.

Because of the tauroursodeoxycholic acid of the present invention excellent solubility in water and exerts cholagogue effect as well as protective effect of hepatocyte, it is useful as a cholestasis ameliorant for the treatment of intrahepatic cholestasis and for the treatment of cholestasis occuring after surgical operation for the treatment of obstructive jaundice.

We claim:

1. A cholestasis ameliorant with an active ingredient consisting of tauroursodeoxycholic acid, wherein said acid is prepared in purified water or physiological saline for injection.

2. A cholestasis ameliorant according to claim 1, wherein the active ingredient is contained at a concentration of 1 to 10% (W/V) in an aqueous solution suitable for injection.

3. A cholestasis ameliorant with an active ingredient consisting of tauroursodeoxycholic acid, in a pharmaceutical preparation suitable for oral administration.

4. A method for the treatment of cholestasis comprising the administration via injection of an effective amount of a composition comprising tauroursodeoxycholic acid in a pharmaceutically acceptable aqueous composition.

5. The method of claim 4 wherein the tauroursodeoxycholic acid is contained at a concentration of 1 to 10% (W/V).

6. A method for the treatment of cholestasis comprising the oral administration of an effective amount of a composition comprising tauroursodeoxycholic acid in a pharmaceutically acceptable composition.

* * * * *